US006795733B1

(12) United States Patent
Lu

(10) Patent No.: US 6,795,733 B1
(45) Date of Patent: Sep. 21, 2004

(54) METHODS AND SYSTEMS FOR AUTOMATICALLY DETERMINING MINUTE VENTILATION

(75) Inventor: Richard Lu, Thousand Oaks, CA (US)

(73) Assignee: Pacesetter, Inc., Sylmar, CA (US)

(*) Notice: Subject to any disclaimer, the term of this patent is extended or adjusted under 35 U.S.C. 154(b) by 358 days.

(21) Appl. No.: 10/103,605

(22) Filed: Mar. 21, 2002

(51) Int. Cl.[7] .......................... A61N 1/368; A61B 5/05; A61B 5/04

(52) U.S. Cl. .......................... 607/17; 600/547; 600/508

(58) Field of Search ............................ 607/17; 600/508, 600/509, 513, 522, 536, 547

(56) References Cited

U.S. PATENT DOCUMENTS 5,282,840 A * 2/1994 Hudrlik ....................... 607/28
5,707,398 A 1/1998 Lu .............................. 607/27
2002/0147475 A1 * 10/2002 Scheiner et al. .............. 607/17

* cited by examiner

*Primary Examiner*—Carl Layno

(57) ABSTRACT

Methods and systems for switching electrode configurations for measuring the transthoracic impedance of patient are described. Various embodiments provide stimulation devices and methods that can automatically adapt to different minute ventilation electrode configurations. This, in turn, permits minute ventilation functionality to continue, e.g. rate-responsive pacing, in spite of the fact that an electrode configuration has changed. Accordingly, minute ventilation functionality can automatically continue in a adaptive manner when a previously-available electrode configuration is no longer available for minute ventilation functionality.

37 Claims, 11 Drawing Sheets

800

802 804

| Priority # | MV Electrode Configuration |
|---|---|
| 1 | Ventricular Bipolar |
| 2 | Atrial Bipolar |
| 3 | Dual Unipolar |
| • | • |
| • | • |
| • | • |
| N | Other |

Fig. 8

METHODS AND SYSTEMS FOR AUTOMATICALLY DETERMINING MINUTE VENTILATION

TECHNICAL FIELD

This invention relates to methods and apparatus for measuring a patient's transthoracic impedance, and more particularly, to techniques for measuring transthoracic impedance for use by a rate-responsive stimulation device.

BACKGROUND

Stimulation devices such as pacemakers are used to treat a variety of cardiac conditions. Some stimulation devices simply provide pacing pulses to a patient's heart at a fixed rate. More sophisticated devices contain sensing circuitry that allows the stimulation devices to monitor a patient's intrinsic signals. For example, some stimulation devices can monitor a patient's atrial heartbeat signals and provide corresponding ventricular pacing pulses, which allows the patient's cardiac output to be adjusted depending on the patient's intrinsic atrial heart rate.

However, there are situations when the heart is not able to regulate its rate appropriately in response to physiological stress. This is known as chronotropic incompetence. Physiologically, the cardiac need of a patient varies depending on the patient's physical activity level. Because of this, so-called rate-responsive stimulation devices have been developed that provide pacing pulses at a rate based on the patient's level of exercise.

Some rate-responsive stimulation devices contain accelerometer-based activity sensors, which assess a patient's level of physical activity by measuring the patient's body movements. When the measured frequency and intensity of a patient's movements are high, the patient's heart is paced at a correspondingly high rate. Although this approach is generally satisfactory, many rate-responsive stimulation devices that use activity sensors are unable to clearly differentiate between body movements due to physical activity and body movements due to external sources (e.g., body movements experienced during an automobile ride).

Other rate-responsive stimulation devices use oxygen sensors to measure a patient's blood-oxygen level. Rate-responsive stimulation devices that use oxygen sensors adjust the pacing rate to maintain a suitable oxygen level. However, oxygen sensors require the use of a special lead.

Another approach that has been used to assess a patient's need for cardiac output is to attempt to determine the amount of air being inhaled and exhaled by the patient. Taking breaths deeply and frequently, for example when climbing the stairs, indicates that there is a high need for cardiac output. Accordingly, if a measure of a patient's air usage can be provided, it can be used for rate-responsive pacing. One measure of a patient's air usage is termed "minute ventilation". Minute ventilation is the total volume of air moved in and out of the lungs in a minute. Transthoracic impedance is measured to calculate minute ventilation and is defined as a measure of the impedance across the chest cavity. More specifically, lungs that are filled with air have a higher impedance than lungs which are empty. Upon inhalation, impedance increases. Upon exhalation, impedance decreases. Minute ventilation is calculated based upon the formula:

Minute Ventilation=Tidal Volume*Respiration Rate

A rate-responsive device measures minute ventilation using the transthoracic impedance, computes a minute ventilation signal, and then compares the current minute ventilation with a long-term average of "change in minute ventilation" to arrive at a required rate.

Consider, for example, FIG. 1 which is a graph of a parameter known as a rate response factor (RRF). The rate response factor can be used to set the expected change in pacing rate in response to increasing changes in minute ventilation during exercise. Each patient has a resting minute ventilation measurement and a maximum minute ventilation measurement. These are respectively indicated on the x-axis as "Resting" and "Peak". Three lines are graphed in FIG. 1 and represent different RRFs relative to a particular patient to whom the graph corresponds. For example, the top line indicates a RRF that is too high for this patient because a maximum metabolic indicated rate is reached before the peak minute ventilation. The bottom line indicates a RRF that is too low for this patient because the maximum metabolic indicated rate is never reached. The middle line indicates an appropriate RRF for this patient because the maximum metabolic indicated rate is reached at the peak minute ventilation.

Before a minute ventilation sensor in a stimulation device can be activated, a baseline impedance measurement for a particular patient needs to be established. This is because the baseline impedance measurement is associated with a minimum pacing rate for that particular patient. The minimum pacing rate for the patient whose graph is shown in FIG. 1 is indicated as the minimum metabolic indicated rate. The minimum pacing rate when the patient is at rest might be around 60 ppm. The maximum pacing rate when, for example, the patient is exercising might be around 150 ppm. These two points are determined, respectively, by the baseline impedance signal (i.e. the signal when the patient is at rest) and the impedance signal when the patient is at maximum exercise. The line between these two points is determined by the rate responsive factor programmed into the stimulation device discussed above.

An advantage of monitoring the impedance of the chest cavity to assess cardiac need is that the stimulation device is less likely to be affected by body movements due to external sources and does not require the use of special leads.

One way for the stimulation device to measure body impedance is to apply a current signal of a known magnitude and waveform across the patient's chest. The resulting voltage signal across the body can be measured by sensing circuitry. The impedance is calculated based on the known magnitude of the applied current signal and the measured magnitude of the voltage signal.

For example, many stimulation devices utilize a ventricular bipolar lead. A ventricular bipolar lead is a lead that is implantable in the ventricle. The lead is bipolar because it is fitted with two electrodes. One of the electrodes is used as the anode, and the other of the electrodes is used as the cathode. In these types of leads, a current signal for measuring impedance can be injected between a ring or coil electrode and the case or "can". A corresponding voltage signal can then be measured between a tip electrode and the case or can, as will be appreciated and understood by those of skill in the art.

One of the problems associated with minute ventilation sensors is that the lead or leads from which impedance measurements are ascertained can sometimes fail to operate as intended. This means that the impedance measurements that are utilized to provide rate-responsiveness can no longer be used to provide this functionality.

Accordingly, this invention arose out of concerns associated with providing improved stimulation devices and methods that provide improved minute ventilation sensors.

SUMMARY

Methods and systems for measuring the transthoracic impedance of patient are described. Various embodiments provide stimulation devices and methods that can automatically adapt to different minute ventilation electrode configurations. This, in turn, permits minute ventilation functionality to continue, e.g. rate-responsive pacing, in spite of the fact that an electrode configuration has changed. Accordingly, minute ventilation functionality can automatically continue in an adaptive manner when a previously-available electrode configuration is no longer available for minute ventilation functionality.

BRIEF DESCRIPTION OF THE DRAWINGS

Further features and advantages of the claimed embodiments can be more readily understood by reference to the following description taken in conjunction with the accompanying drawings, in which:

FIG. 8 is a block diagram of an exemplary table in accordance with one embodiment.

DETAILED DESCRIPTION

The following description is of the best mode presently contemplated for practicing the described embodiments. This description is not to be taken in a limiting sense, but rather is made merely for the purpose of describing the general principles of the inventive embodiments. The scope of the described embodiments should be ascertained with reference to the issued claims. In the description of the embodiments that follow, like numerals or reference designators will be used to refer to like parts or elements throughout.

Overview

The methods and systems described below provide stimulation devices and methods that can automatically adapt to different minute ventilation electrode configurations. This, in turn, permits minute ventilation functionality to continue, e.g. rate-responsive pacing, in spite of the fact that an electrode configuration has changed. Accordingly, minute ventilation functionality can automatically continue in an adaptive manner when a previously-available electrode configuration is no longer available for minute ventilation functionality.

Exemplary Stimulation Device

The techniques that are described below are intended to be implemented in connection with a stimulation device that is configured or configurable to stimulate or shock a patient's heart.

Figure 2:
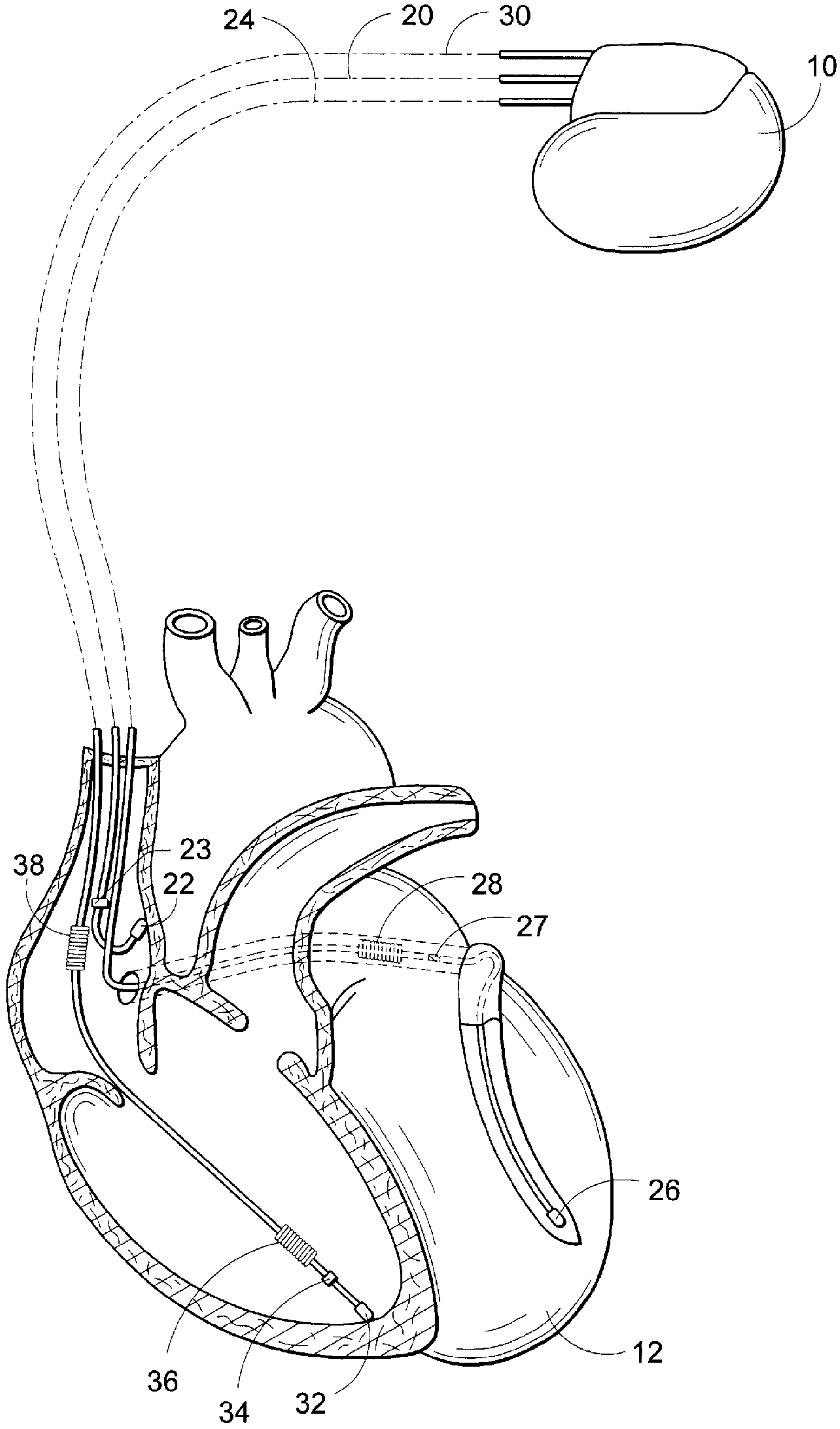
FIG. 2 is a simplified diagram illustrating an implantable stimulation device in electrical communication with at least three leads implanted into a patient's heart for delivering multi-chamber stimulation and shock therapy.

FIG. 2 shows an exemplary stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, stimulation device 10 is coupled to an implantable right atrial lead 20 having at least an atrial tip electrode 22, which typically is implanted in the patient's right atrial appendage. The right atrial lead can also have a ring electrode 23 positioned above the atrial tip electrode 22.

To sense left atrial and ventricular cardiac signals and to provide left chamber pacing therapy, stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

Stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 3:
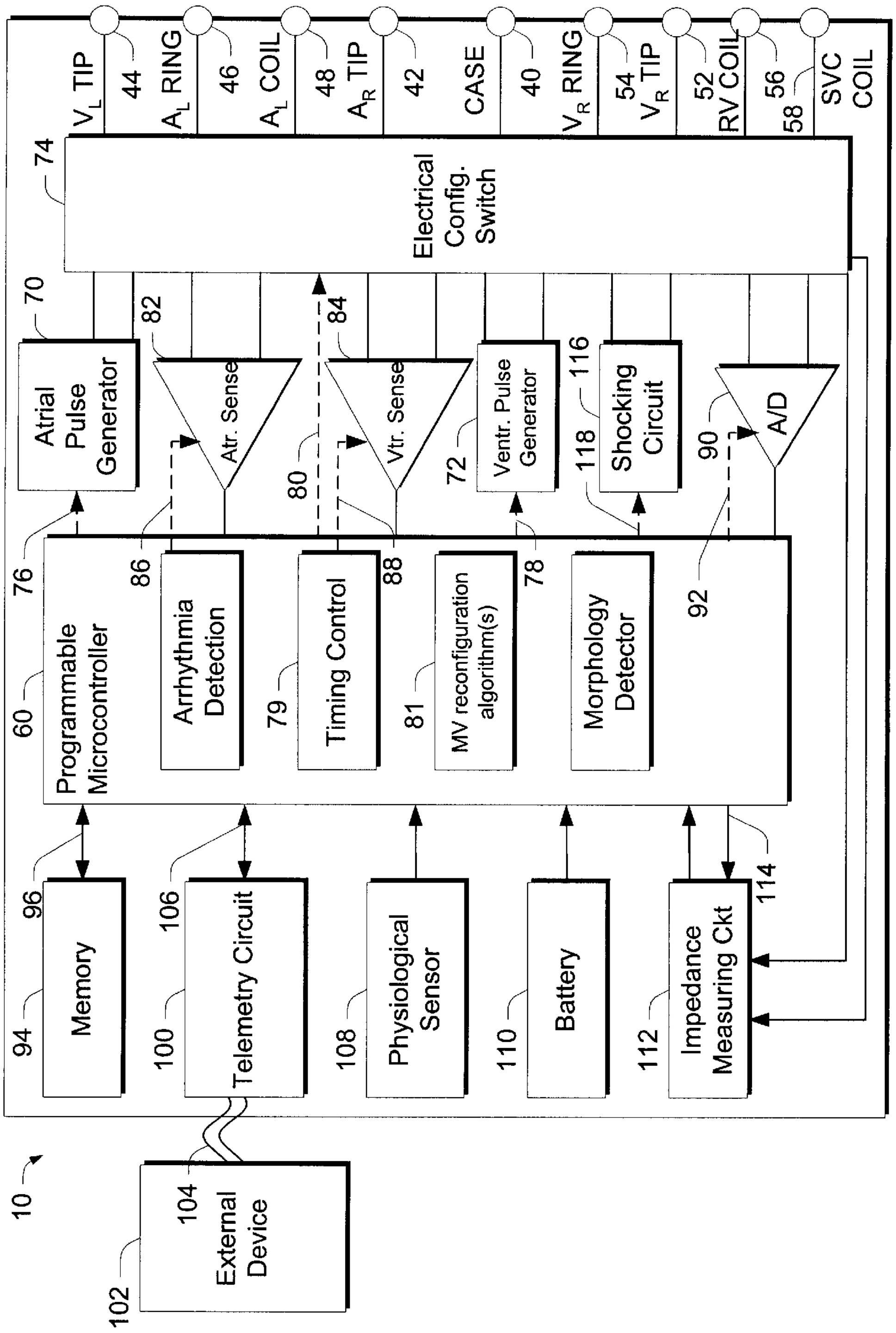
FIG. 3 is a functional block diagram of a multi-chamber implantable stimulation device illustrating the basic elements of a stimulation device which can provide cardioversion, defibrillation and pacing stimulation in four chambers of the heart.

FIG. 3 shows an exemplary, simplified block diagram depicting various components of stimulation device 10. The stimulation device can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the inventive techniques and methods described below can be implemented in connection with any suitably configured or configurable stimulation device. Accordingly, one of skill in the art could readily duplicate, eliminate or disable the appropriate circuitry in any desired combination to provide a device capable of treating the appropriate chamber(s) with cardioversion, defibrillation and pacing stimulation.

Housing 40 for stimulation device 10 is often referred to as the "can", "case" or "case electrode", and may be programmably selected to act as the return electrode for all "unipolar" modes. There may be multiple electrode positioned on or otherwise supported by the housing. The multiple electrodes can be used for impedance measurements, as will become apparent below. Housing 40 may further be used as a return electrode alone or in combination with one or more of the coil electrodes, 28, 36 and 38, for shocking purposes. Housing 40 further includes a connector (not shown) having a plurality of terminals 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design and operation of the microcontroller 60 are not critical to the described embodiments. Rather, any suitable microcontroller 60 may be used that carries out the functions described herein. The use of microprocessor-based control circuits for performing timing and data analysis functions are well known in the art.

FIG. 3 also shows an atrial pulse generator 70 and a ventricular pulse generator 72 which generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

Microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 60 further includes one or more minute ventilation reconfiguration algorithms 81 that can be utilized by the stimulation device 10 for automatically reconfiguring various electrode configurations that are used to ascertain impedance which, in turn, is used to calculate a patient's minute ventilation.

A switch 74 includes a plurality of switches for connecting the desired electrodes to the appropriate I/O circuits, thereby providing complete electrode programmability. Accordingly, switch 74, in response to a control signal 80 from the microcontroller 60, determines the polarity of the stimulation pulses (e.g., unipolar, bipolar, combipolar, etc.) by selectively closing the appropriate combination of switches (not shown). The switch 74 can also be used by the microcontroller 60 to reconfigure electrode configurations that are used for determining minute ventilation responsive to the minute ventilation reconfiguration algorithms 81.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. One feature of the described embodiments is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 can further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer (e.g. a three-dimensional accelerometer) or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the described embodiments and is shown only for completeness.

The described embodiments can utilize a "sleep state" or diurnal sensor that can detect sleep, rest, and wake states. One such sensor is known as "activity variance" wherein an activity sensor is monitored diurnally to detect the low variance in the measurement corresponding to the sleep state.

The stimulation device additionally includes a battery 110 that provides operating power to all of the circuits shown in FIG. 3. For the stimulation device 10, which employs shocking therapy, the battery 110 is capable of operating at low current drains for long periods of time (e.g. preferably less than 10 $\mu$A), and is capable of providing high-current pulses (for capacitor charging) when the patient requires a shock pulse (e.g. preferably, in excess of 2 A, at voltages above 2 V, for periods of 10 seconds or more). The battery 110 also desirably has a predictable discharge characteristic so that elective replacement time can be detected. Accordingly, the device 10 preferably employs lithium/silver vanadium oxide batteries, as is true for most (if not all) current devices.

The stimulation device 10 can further include magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

FIG. 3 also shows an impedance measuring circuit 112 which is enabled by the microcontroller 60 via a control signal 114. Uses for an impedance measuring circuit 120 can include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc.

In the embodiments described below, the impedance measuring circuit 112 is additionally used to ascertain when a particular electrode configuration that is used for ascertaining minute ventilation (i.e. ascertaining impedance which is then used to ascertain minute ventilation as described above) is no longer able to reliably function in this capacity. The impedance measuring circuit 120 is advantageously coupled to the switch 74 so that any desired electrode may be used.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Exemplary Minute Ventilation Electrode Configurations

As noted above, to ascertain a patient's minute ventilation the thoracic or transthoracic impedance is determined. There are various electrode configurations that can be utilized to ascertain this impedance measure. As will be understood by those of skill in the art, the transthoracic impedance is different from the lead impedance associated with determining lead electrode integrity.

Figure 4:
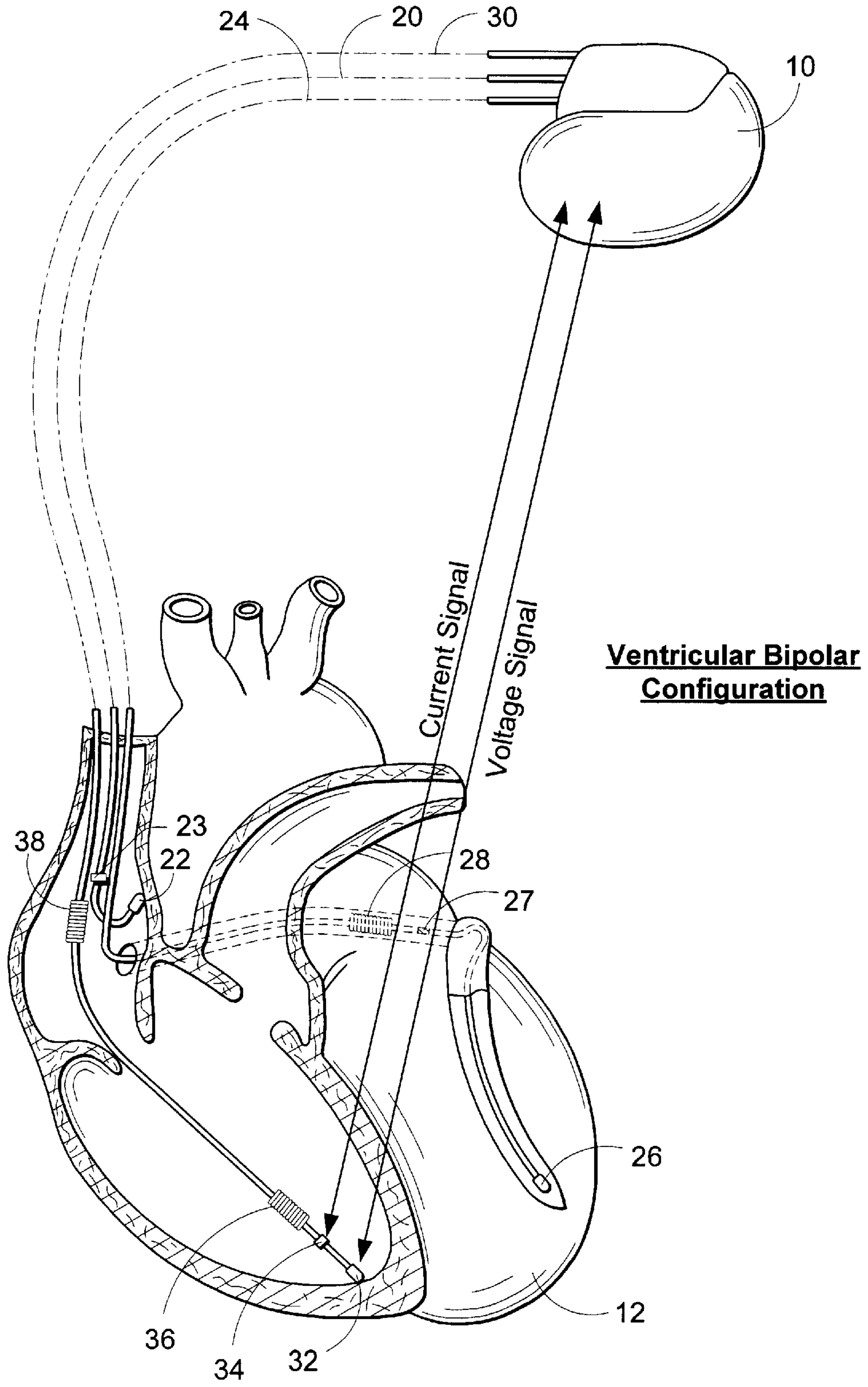
FIG. 4 is a diagram that shows one exemplary minute ventilation electrode configuration.

FIG. 4 shows one electrode configuration referred to as a "ventricular bipolar configuration". In this configuration, a ventricular bipolar lead is used. Electrical current signals are injected between ring electrode 34 and the can or case. Corresponding voltage signals are measured between the tip electrode 32 and the can or case. The impedance can then be calculated from the measured signals. From the impedance measure, the minute ventilation can be derived.

Figure 5:
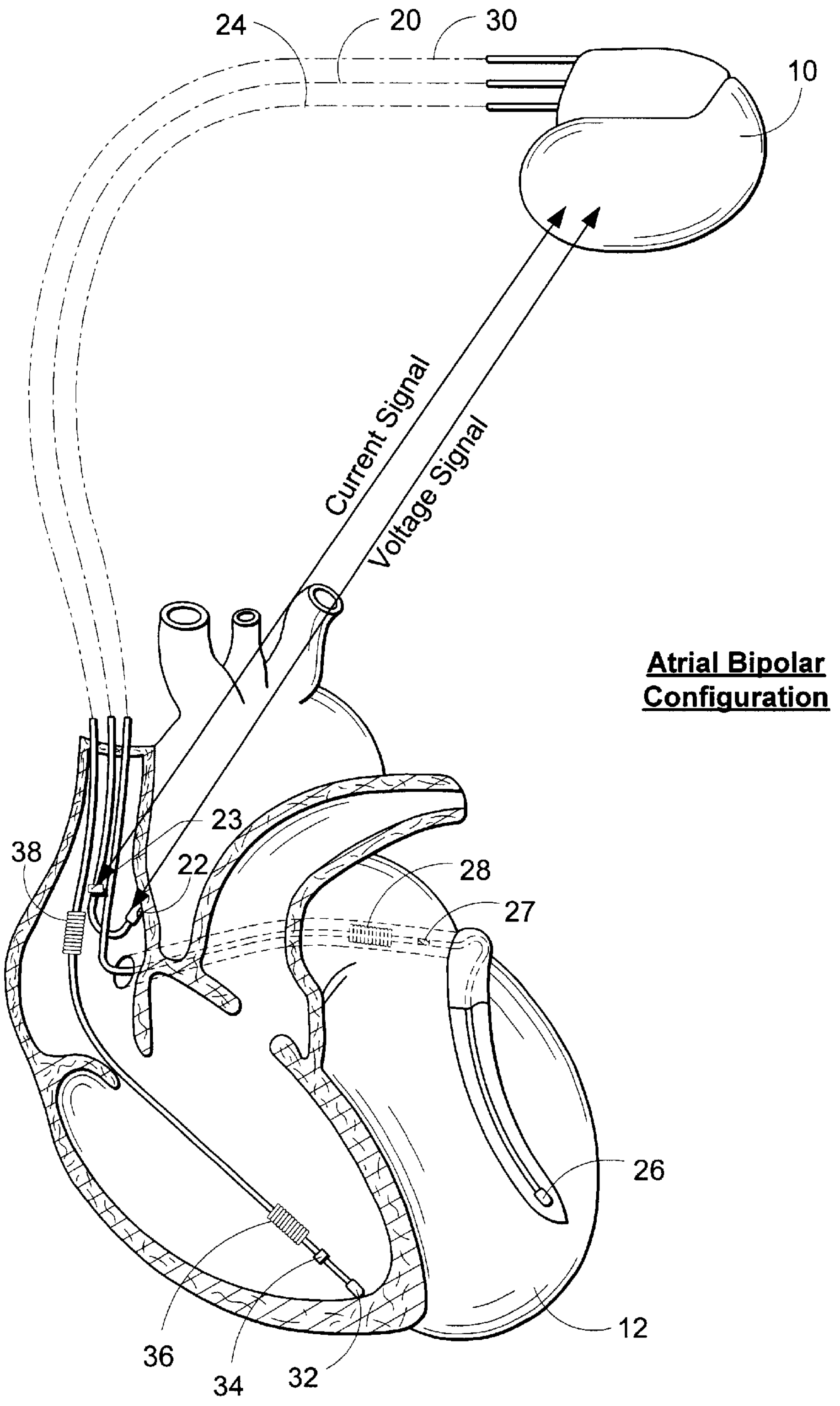
FIG. 5 is a diagram that shows one exemplary minute ventilation electrode configuration.

FIG. 5 shows another electrode configuration referred to as an "atrial bipolar configuration". In this configuration, an atrial bipolar lead is used. Electrical current signals are injected between the ring electrode 23 and the can or case. Corresponding voltage signals are measured between the tip electrode 22 and the can or case. The impedance can then be calculated from these two signals. From the impedance measure, the minute ventilation can be derived.

Figure 6:
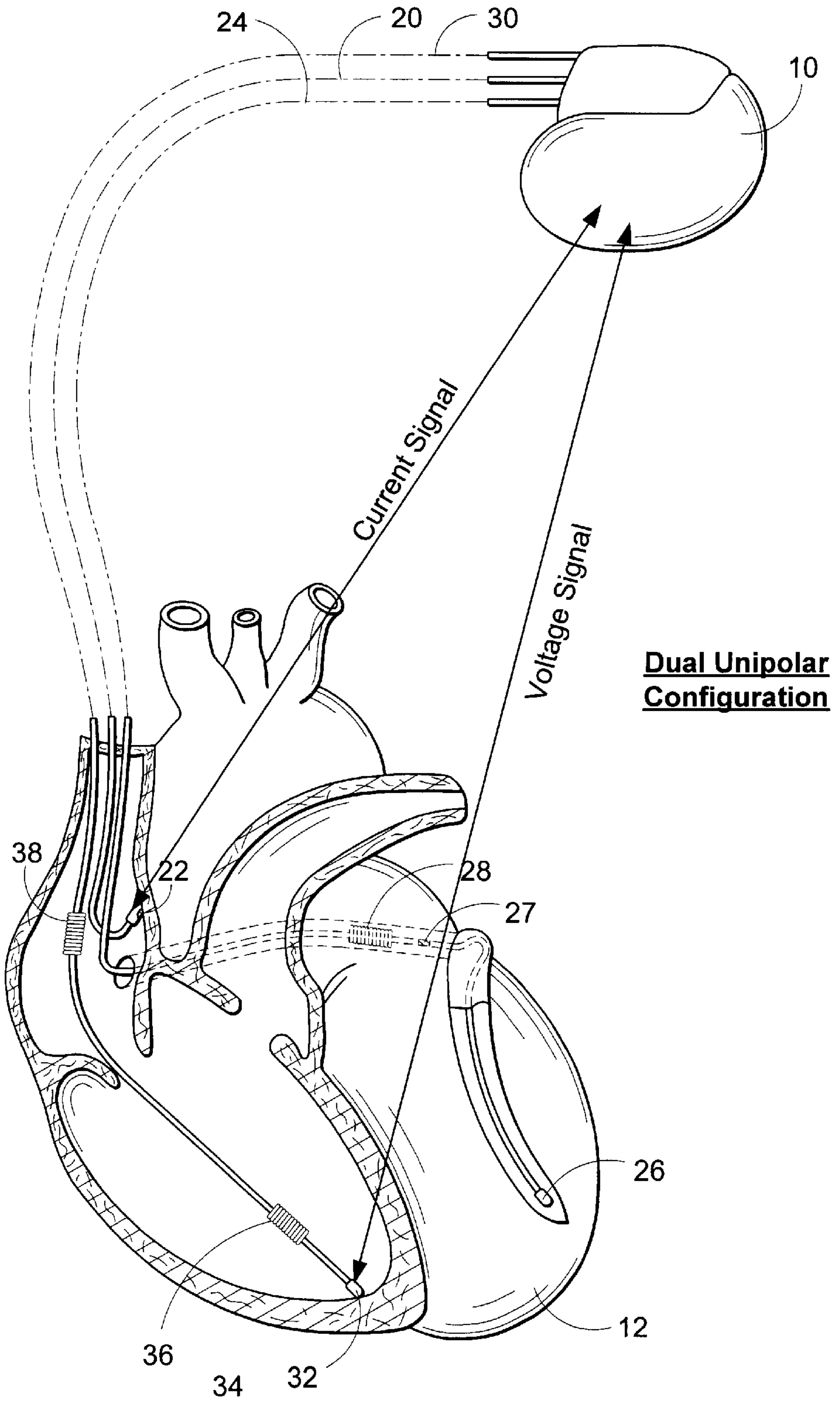
FIG. 6 is a diagram that shows one exemplary minute ventilation electrode configuration.

FIG. 6 shows another electrode configuration referred to as a "dual unipolar configuration". In this configuration, the atrial and ventricular leads are unipolar leads. Electrical current signals are injected between the atrial tip electrode 22 and the can or case. Corresponding voltage signals are measured between the ventricular tip electrode 32 and the can or case. The impedance can then be calculated from these two signals. From the impedance measure, the minute ventilation can be derived.

Other minute ventilation electrode configurations can, of course be used. For example, multiple electrodes (e.g. dot electrodes) can be provided on the can or case so that a single unipolar ventricular or atrial lead can be used to inject current signals, and can serve as an electrode relative to which a voltage signal is measured from the can or case. An example of such an electrode configuration is shown and described in U.S. patent application Ser. No. 09/326,939, entitled "Minute Volume Pacemakers that Require Only a Single Distal Electrode", filed on Jun. 7, 1999, naming Richard Lu as inventor, the disclosure of which is incorporated by reference herein.

FIGS. 4–6 and the discussion in this section are intended to illustrate exemplary non-limiting electrode configurations that can be used for ascertaining minute ventilation. It is to be appreciated and understood that other electrode configurations could be used. For example, other configurations can include shock electrodes in an ICD system. In addition, it may be likely that in the future additional electrode configurations (including new and/or additional electrodes) for use in determining minute ventilation will be conceived and developed. It should be readily apparent that the principles about to be described below can be applied to these other additional electrode configurations. A key consideration in such other configurations is to have the two electrodes (for current injection or impedance measurements) span across the lung.

Exemplary Methods for Determining Minute Ventilation

Figure 7:
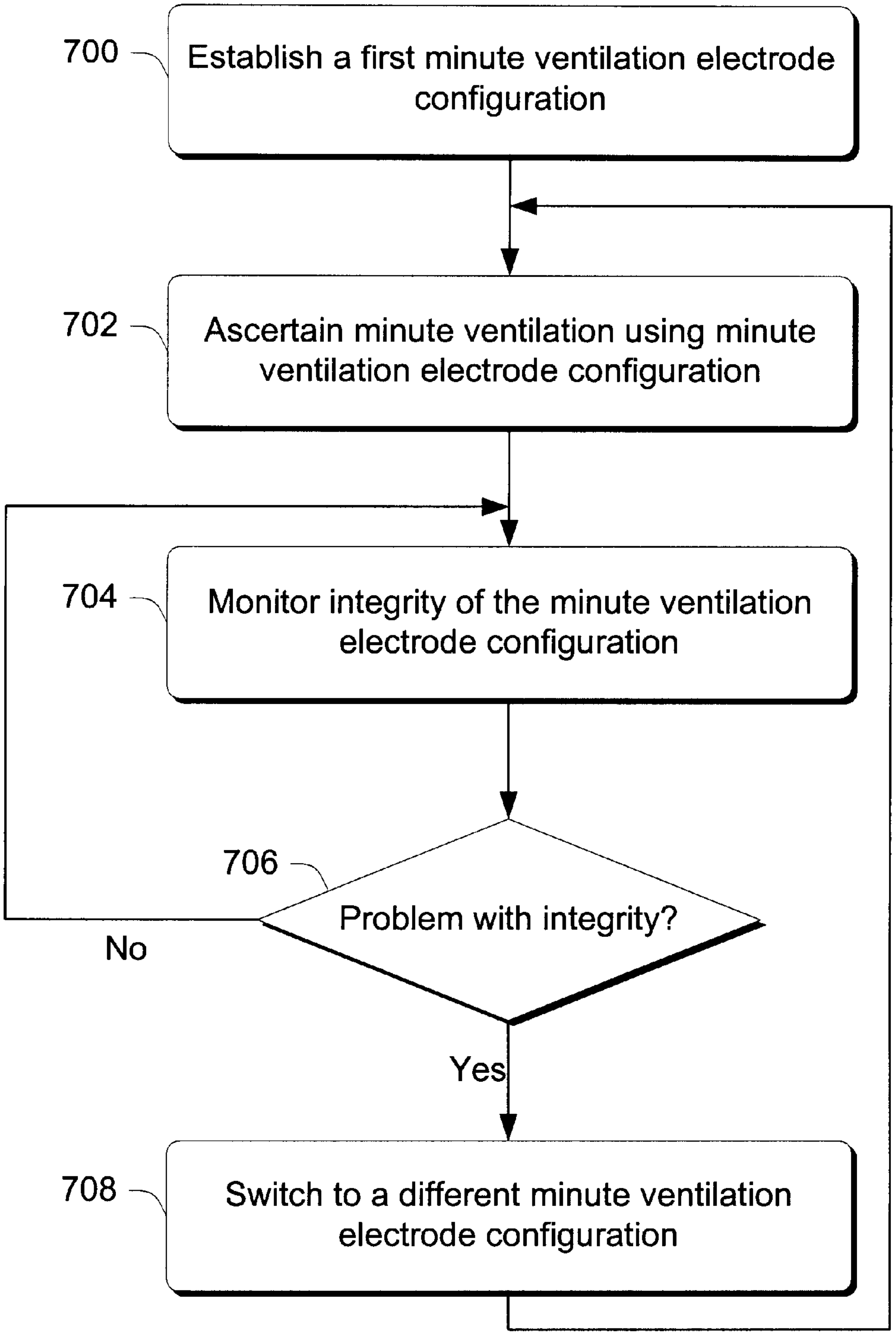
FIG. 7 is a flow diagram that describes steps in a method in accordance with one embodiment.

FIG. 7 shows a flow diagram that describes steps in a method in accordance with one embodiment. The method can be implemented in any suitable hardware, software, firmware, or combination thereof. In the illustrated embodiment, the method is implemented in both hardware and software.

Step 700 establishes a first minute ventilation electrode configuration. Any electrode configuration that is suitable for use in determining minute ventilation can be used. The electrode configuration is desirably programmatically established by a suitably programmed stimulation device. Several examples of minute ventilation electrode configurations are given above. One example of a stimulation device is given above. Other stimulation devices can, of course, be utilized to establish the first minute ventilation electrode configuration.

Step 702 then ascertains minute ventilation using the minute ventilation electrode configuration. This step can be implemented in any suitable way. In the examples given above, the electrode configurations are used to ascertain a thoracic impedance measurement which, in turn, can be used to determine a tidal volume meter and a respiration rate parameter. These two parameters can then be to derive minute ventilation.

Step 704 monitors the integrity of the minute ventilation electrode configuration. Any suitable techniques can be utilized to monitor the integrity of the configuration. For example, known lead supervision techniques can be used to monitor the impedance of the leads. Step 706 determines whether there is a problem with the integrity of the monitored electrode configuration. For example, if lead supervision techniques are used, then this step can be implemented by determining whether the impedance of the current injection electrodes (e.g. ring to case) and the impedance measurement electrodes (e.g. tip to case) fall outside a range of normal operating values. Alternately, this step can be implemented by ascertaining whether the impedances of the electrodes involved change by a pre-determined amount or percentage (thus possibly indicating a faulty lead). If there are no perceived integrity problems with the current electrode configuration, the method branches back to step 704 and continues to monitor the configuration integrity. If, on the other hand, step 706 determines that there is an integrity problem with the current electrode configuration, then step 708 switches to a different minute ventilation electrode configuration. This step is desirably automatically implemented by the stimulation device. Several different minute ventilation electrode configurations are described above. Step 708 then branches back to step 702 which then ascertains the minute ventilation using the new minute ventilation electrode configuration. Step 702 can involve some baseline calibration operations which are described in more detail below in a section entitled "Re-establishing the Baseline".

In the FIG. 3 example given above, one or more minute ventilation reconfiguration algorithms 81 reside in the microcontroller 60. These algorithms can receive input from the impedance measuring circuit 112. Recall that the impedance measuring circuit can continuously measure the impedance of the leads that are implanted in the patient. If the minute ventilation algorithm(s) determine that the measured impedance of one or more of the leads is problematic, the algorithms 81 can cause microcontroller 60 to provide an input to switch 74 via line 80. This input can cause the switch 74 to reconfigure the minute ventilation electrode configuration.

Minute Ventilation Electrode Configuration Priorities

In some embodiments, a stimulation device can be configured such that multiple different alternate minute ventilation electrode configurations are possible. That is, in addition to a first configuration, there can be additional different configurations that are possible for selection in the event that the first configuration has integrity problems.

As an example, consider FIG. 8. There, a minute ventilation (MV) configuration table 800 is shown. The MV configuration table 800 can be maintained on the stimulation device so that the stimulation device can use it if the need arises. Table 800 includes two columns 802, 804. Column 802 is a priority number column and contains a value that is associated with the priority of a particular MV electrode configuration. Column 804 contains an entry that corresponds to a particular MV electrode configuration. In this specific example, the stimulation device is configured so that it can implement, if necessary, the following configurations: ventricular bipolar, atrial bipolar, dual unipolar, and one or more "other" configurations. Each of these particular configurations carries with it a priority. Specifically, the ventricular bipolar configuration has the highest priority followed respectively by the atrial bipolar configuration, the dual unipolar configuration and the "other" configuration(s). If the next configuration is available, a check can be made to ensure that the configuration is operable. An impedance measurement can be used to check the operability. In operation (in this example), minute ventilation will be ascertained using first, the ventricular bipolar configuration. If an integrity problem develops with this configuration, then the electrode configuration will be switched to the next-in-line configuration which, in this case, is the atrial bipolar configuration, and so on.

Each stimulation device is desirably knowledgeable of the leads and lead types that it has in place, and can thus be programmed with a table that has the established priorities. If the stimulation device does not have a particular lead configuration that permits a particular MV electrode configuration in the table, then that particular configuration can be removed or otherwise nullified from the table. The table can also be automatically generated at implant and periodically confirmed for availability, or it can be specifically programmed by, for example, a physician who desires to implement a specific combination of electrode configurations that, for whatever reason, are desirable for a particular patient.

Figure 9:
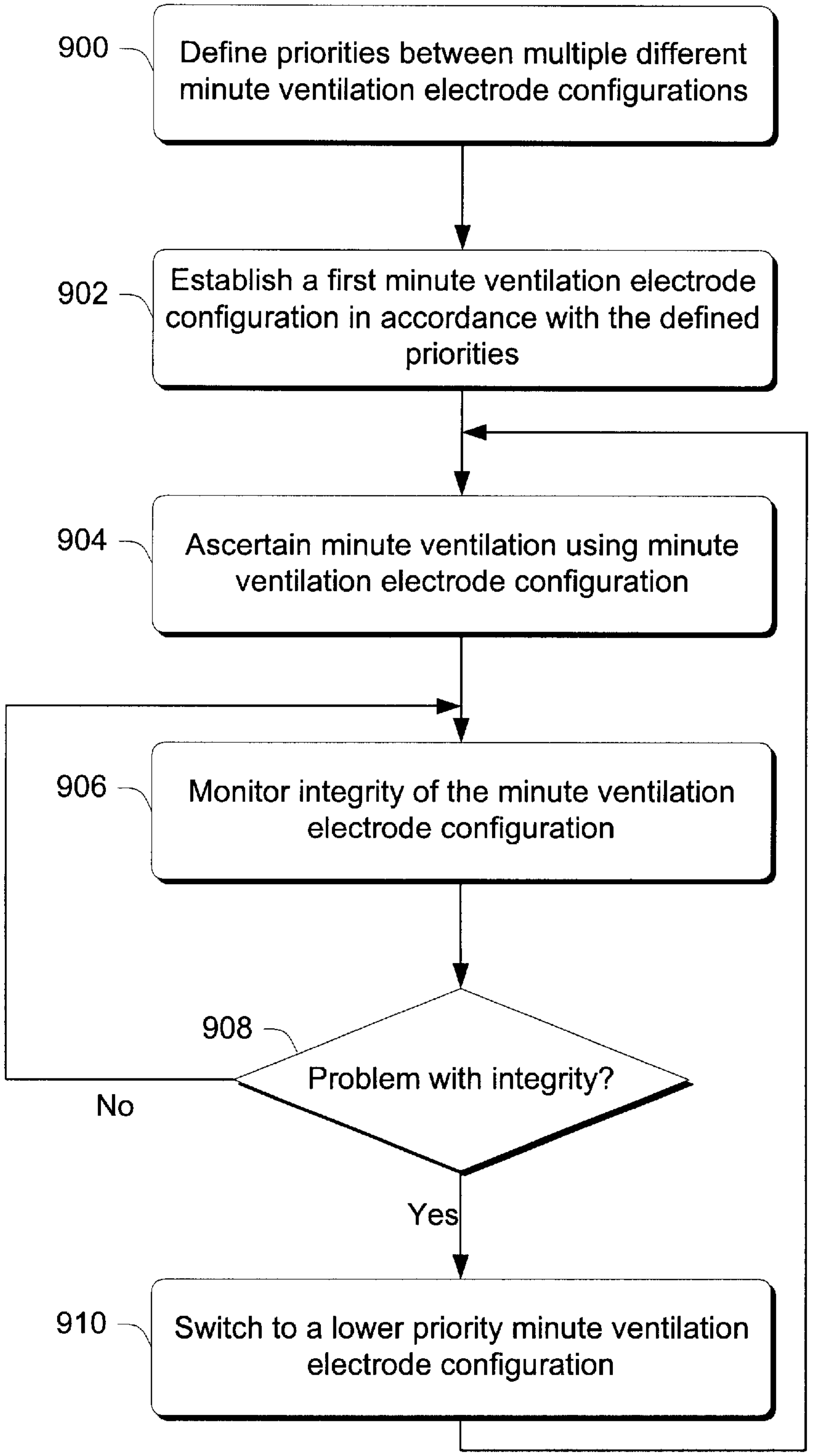
FIG. 9 is a flow diagram that describes steps in a method in accordance with one embodiment.

FIG. 9 shows a flow diagram that describes steps in a method in accordance with one embodiment. The method can be implemented in any suitable hardware, software, firmware, or combination thereof. In the illustrated embodiment, the method is implemented in both hardware and software.

Step 900 defines priorities between multiple different minute ventilation electrode configurations. This step can be implemented in several different ways. For example, individual stimulation devices can be pre-programmed to support many of a potentially large number of electrode configurations that can be utilized to ascertain minute ventilation. The stimulation devices can then, at some later time, ascertain which of the leads they are equipped with and then pare down the possible configurations to only those that are specifically supported by the lead arrangement connected to the stimulation device. The priorities and their associated configurations can be maintained in any suitable manner, such as with a table like the one described in FIG. 8. Alternately, stimulation devices can be programmed to support only a desired number of configurations which might be less then the total number of possible configurations that the devices can support.

Step 902 establishes a first minute ventilation electrode configuration in accordance with the defined priorities. Any electrode configuration that is suitable for use in determining minute ventilation can be used. Examples of minute ventilation electrode configurations that can be established in accordance with defined priorities are given in FIG. 8.

Step 904 then ascertains minute ventilation using the established minute ventilation electrode configuration. This step can be implemented in any suitable way. In the examples given above, the electrode configurations are used to ascertain a thoracic impedance measurement which, in turn, can be used to determine a tidal volume parameter and a respiration rate parameter. These two parameters can then be used to derive minute ventilation.

Step 906 monitors the integrity of the minute ventilation electrode configuration. Any suitable techniques can be utilized to monitor the integrity of the configuration, with examples being given above. Step 908 determines whether there is a problem with the integrity of the monitored electrode configuration. If there are no perceived integrity problems with the current electrode configuration, the method branches back to step 906 and continues to monitor the configuration integrity. If, on the other hand, step 908 determines that there is an integrity problem with the current electrode configuration, then step 910 switches to a lower priority minute ventilation electrode configuration. This step is desirably automatically implemented by the stimulation device. Step 910 then branches back to step 904 which then ascertains the minute ventilation using the new minute ventilation electrode configuration. Step 904 can involve some baseline calibration operations which are described in more detail below in a section entitled "Re-establishing the Baseline".

Re-establishing the Baseline Impedance

Recall that a baseline impedance measurement is utilized to establish a rate response factor (RRF) that is used to rate-responsively pace a patient. When the minute ventilation electrode configuration is changed, the baseline impedance measurement that was previously used is no longer valid. Accordingly, the baseline impedance is re-calculated or re-established so that it can be used with the new electrode configuration.

Figure 10:
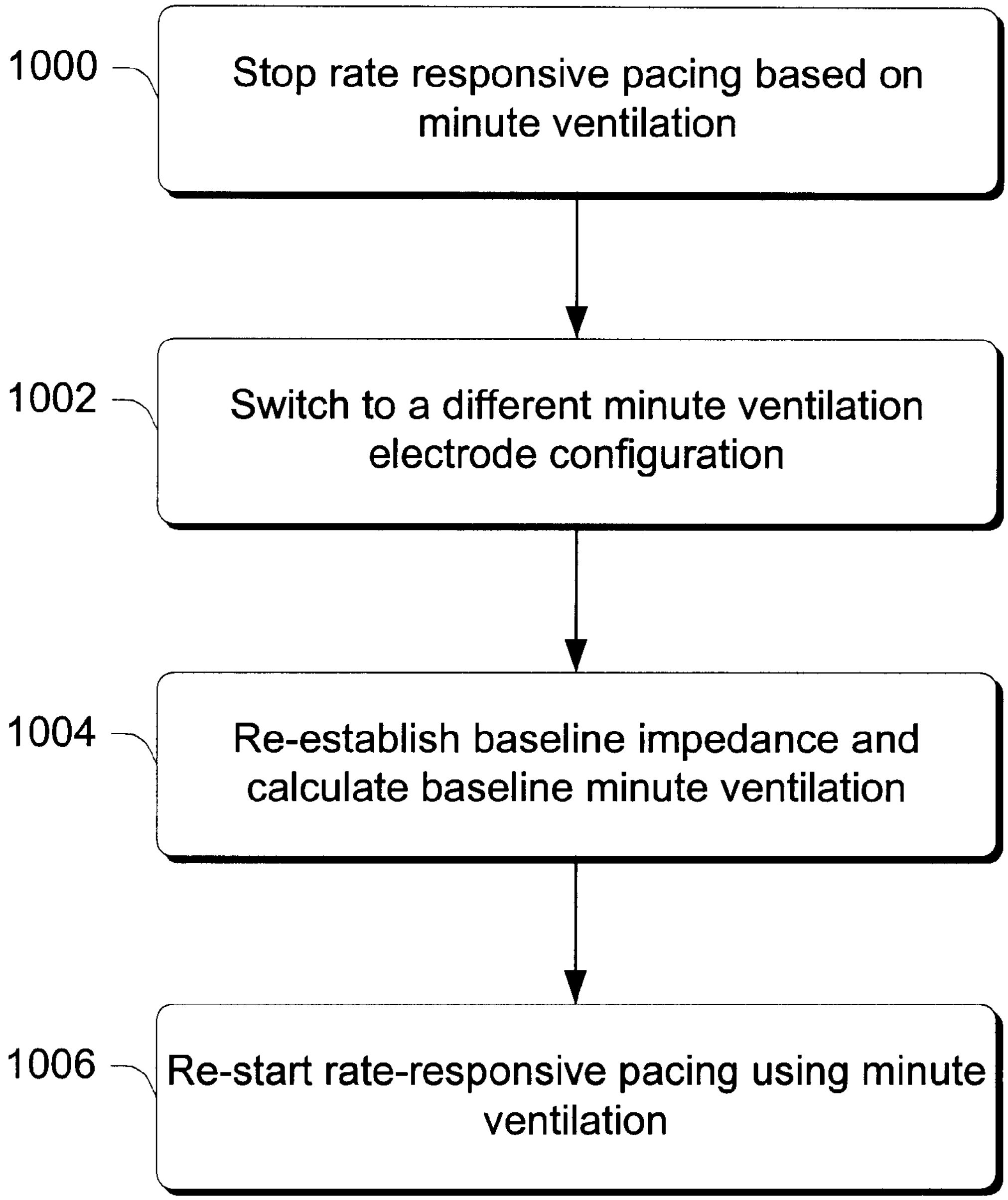
FIG. 10 is a flow diagram that describes steps in a method in accordance with one embodiment.

FIG. 10 is a flow diagram that describes steps in a method in accordance with one embodiment. The method can be implemented in any suitable hardware, software, firmware, or combination thereof. In the illustrated embodiment, the method is implemented in both hardware and software. The method about to be described can take place typically when the stimulation device ascertains that there is an integrity problem with the current minute ventilation electrode configuration. This corresponds to the "Yes" branches of step 706 in FIG. 7 and step 908 in FIG. 9.

When an integrity problem with a current minute ventilation electrode configuration is detected, part of the processing that can take place is that step 1000 can stop the rate-responsive pacing that is based on minute ventilation. At this point, the device can be placed in a non-rate responsive mode to pace at a fixed rate delivered through a selected pacing configuration and in a mode where it can operate to measure the patient's transthoracic impedance. Step 1002 then switches to a different minute ventilation electrode configuration. This step can be implemented in any of the ways described above. The device can now be used in its impedance measuring mode to measure the patient's transthoracic impedance using the new electrode configuration.

Figure 1:
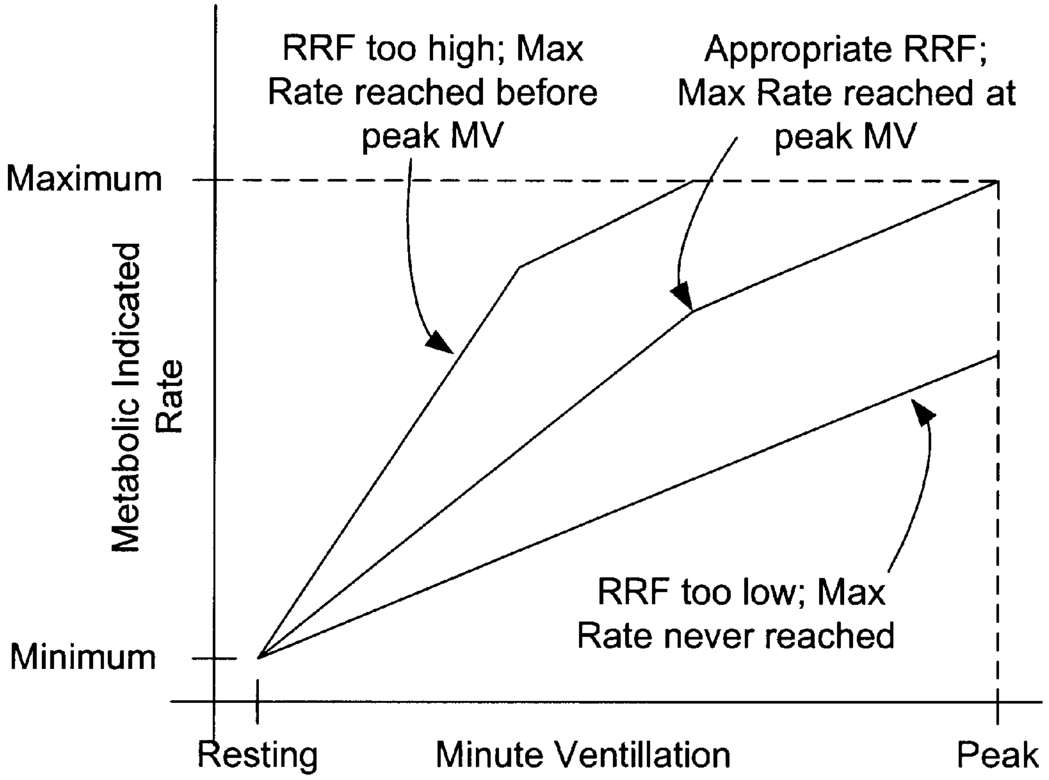
FIG. 1 is a graph that is useful in understanding aspects of the described embodiments.

Step 1004 re-establishes the baseline transthoracic impedance and calculates the baseline minute ventilation (see FIG. 1). This step can be implemented in a couple of different ways. For example, a minute ventilation sensor can typically require a baseline acquisition while the patient is at rest for a pre-determined period of time, e.g. 3 minutes. The minute ventilation sensor will not typically reinitiate rate-responsive pacing until this is done. Hence, in one embodiment, a patient may be required to remain physically at rest for the pre-determined period of time. In yet other embodiments, baseline impedance values can be re-established by using one or more activity sensors that are onboard the stimulation device. Specifically, if an activity sensor is available, the stimulation device can monitor for a time period during which the patient's activity levels have not exceeded a certain threshold. The device can then use transthoracic impedance measurements taken during this time period for establishing the baseline impedance.

In yet other embodiments, an activity sensor may not be available for use. In this case, the stimulation device can use an adaptive approach to re-establishing the baseline impedance. For example, the stimulation device can adapt for a pre-determined period of time, e.g. one hour, before the baseline impedance values are written into the storage devices that are used for minute ventilation.

After the baseline impedance measure is re-established by step 1004, step 1006 re-starts rate-responsive pacing using the new electrode configuration to determine minute ventilation.

Figure 11:
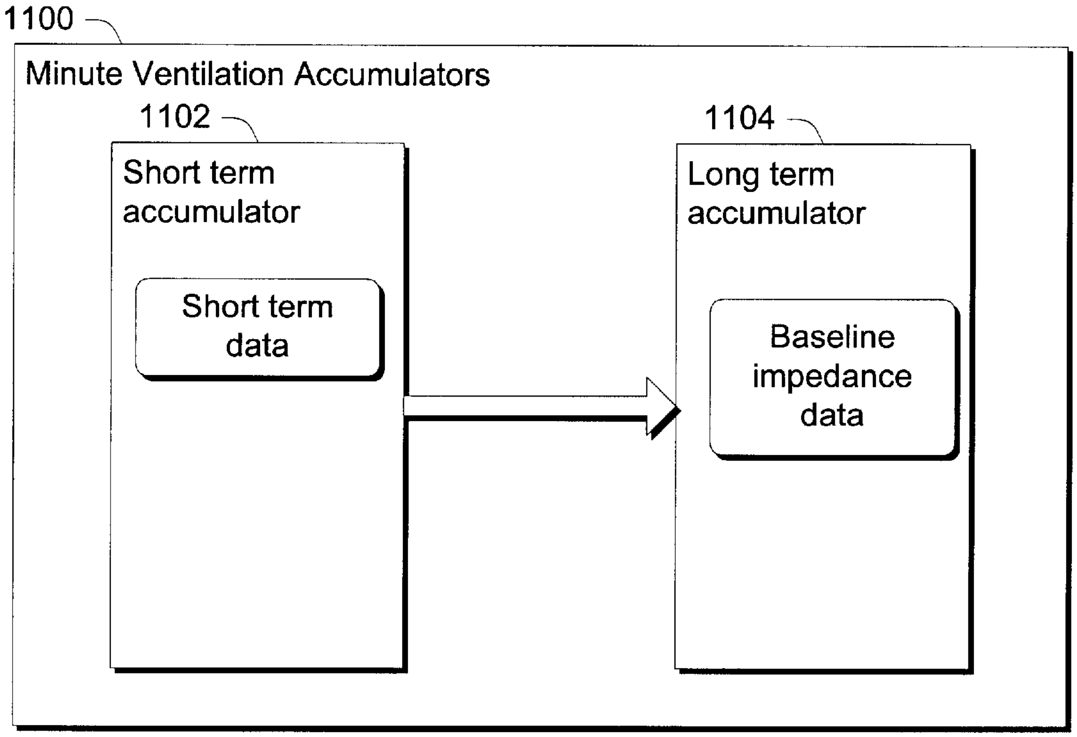
FIG. 11 is a block diagram that illustrates exemplary minute ventilation accumulators in accordance with one embodiment.

As a practical matter of how the new baseline impedance measurements can be calculated, in but one example, consider FIG. 11. There, minute ventilation accumulators 1100 comprises a short term accumulator 1102 and a long term accumulator 1104. Accumulators 1100 can be implemented as storage devices, i.e. computer-readable media, on board the stimulation device. Short term accumulator 1102 contains short term data that corresponds to measurements of an impedance signal over the short or near term. Long term accumulator 1104 contains data that is the baseline impedance data that is associated with a particular minute ventilation electrode configuration. Essentially, the impedance signals are measured or calculated and stored in the accumulators. The short term accumulator 1102 will eventually get copied into the long term accumulator 1104. The difference between the two accumulators is that they are associated with different time constants. To do rate response pacing, a difference between data in the short term accumulator and the long term accumulator is calculated to determine a rate at which to pace the patient. Accordingly, the assumption in this example is that long term accumulator 1104 holds the base line impedance data and the short term accumulator 1102 holds data that is associated with current patient activity, e.g. when the patient starts exercising.

EXAMPLE

As an example of how the above methods and systems can be used to automatically continue rate responsive pacing using minute ventilation when, for example, a polarity switch occurs on the leads of a stimulation device, consider the following.

In this example, a lead supervision feature on the stimulation device continuously monitors the integrity of the leads. This is desirably done by monitoring the impedance of the leads and determining whether the lead impedance remains within an operable range. When the lead impedance extends outside the operable range, it is desirable to change the polarity of the leads. This may entail changing from a bipolar configuration to a unipolar configuration. If the patient is receiving rate-responsive pacing, it is desirable to continue the rate-responsiveness. As noted above, however, the transthoracic impedance measurements that serve to define the impedance baseline for the minute ventilation sensor will likely need to be re-calculated as a result of the polarity change.

Assume now that the lead supervision feature indicates that a polarity switch criteria are met (i.e. there is another polarity to which the device can be switched), the current ventricular pacing configuration is bipolar, and the current minute ventilation configuration is also ventricular bipolar. In this case, the following procedure can be followed. First, the minute ventilation sensor can be temporarily turned off.

This can entail turning off the rate-responsive functionality associated with the sensor, but allowing the sensor to operate in a mode that permits the transthoracic impedance to be determined. The stimulation device can now select an alternative minute ventilation electrode configuration if there is one available. In this example, assume that the patient has an atrial bipolar lead. Hence, the atrial bipolar minute ventilation electrode configuration can be selected. If the atrium has a unipolar lead, the next alternate configuration after the atrial bipolar configuration would be a dual unipolar configuration. In high voltage or multiple chamber (i.e. more than two) devices, other alternatives are also available. For example, current can be injected through the right ventricle shock electrode to the case. Transthoracic impedance measurements can be made through the ventricular tip electrode to the case. Alternately, current injection can occur through the atrial shock electrode to the case, and impedance measurements can be made between the ventricle shock electrode and the case.

Once the new configuration has been selected, impedance measurements can now be performed to ascertain the new impedance baseline. Non-limiting examples of ways that this can be done are given above. Once the baseline impedance measurements are established, the minute ventilation sensors can be returned to a mode in which it can be used for rate-responsive pacing.

Patient Notification if no Alternate Minute Ventilation Configuration

In the event that the minute ventilation sensor is the only rate responsive sensor in the stimulation device and an alternative minute ventilation electrode configuration is not available (e.g. perhaps only a ventricular lead is implanted and a single unipolar configuration for minute ventilation measurements is not available), the patient can be notified that the rate-responsive function is not enabled. Notification can take place, for example, through a slight electrical stimulation that causes a muscle twitch in the patient. In this case, the stimulation device can fallback to a fixed-rate. Notification can also take place through the use of an audio alarm.

Conclusion

The various embodiments described above provide stimulation devices that can automatically adapt to different electrode configurations that permit minute ventilation-dependent rate-responsive pacing to continue in spite of the fact that an electrode configuration has changed. This is advantageous from the standpoint of being able to continue minute ventilation functionality when a previously-available electrode configuration is no longer available for minute ventilation functionality. In addition, the configuration change can be recorded in the device so that the clinician can be informed as soon as possible (e.g. at the next follow up or through other means such as a remote monitor).

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

What is claimed is:

1. A method for ascertaining minute ventilation comprising:

providing a programmable stimulation device having multiple electrodes; and programming the stimulation device with code which, when executed by the stimulation device is configured to cause the stimulation device to:

establish a first electrode configuration sufficient for use in ascertaining a patient's minute ventilation;

ascertain the patient's minute ventilation using the first electrode configuration;

monitor the integrity of the first electrode configuration; and responsive to a problem with the integrity of the first electrode configuration, switch to a different electrode configuration sufficient for use in ascertaining the patient's minute ventilation.

2. The method of claim 1, wherein the first electrode configuration comprises a ventricular bipolar configuration.

3. The method of claim 1, wherein the different electrode configuration comprises one or more of an atrial bipolar configuration and a dual unipolar configuration.

4. The method of claim 1, wherein the first electrode configuration comprises a bipolar configuration and the different electrode configuration comprises a unipolar configuration.

5. The method of claim 1, wherein said monitoring comprises monitoring one or more electrode impedances associated with leads that carry electrodes defining the first electrode configuration.

6. A method for ascertaining minute ventilation comprising:

providing a stimulation device having multiple electrodes; and configuring the stimulation device to:

establish a first electrode configuration sufficient for use in ascertaining a patient's minute ventilation;

ascertain the patient's minute ventilation using the first electrode configuration;

monitor the integrity of the first electrode configuration; and responsive to a problem with the integrity of the first electrode configuration, switch to a different electrode configuration sufficient for use in ascertaining the patient's minute ventilation.

7. A stimulation device comprising:

one or more computer-readable media;

one or more processors; and instructions stored on the computer-readable media which, when executed by the one or more processors, cause the processors to:

establish a first electrode configuration sufficient for use in ascertaining a patient's minute ventilation;

ascertain the patient's minute ventilation using the first electrode configuration;

monitor the integrity of the first electrode configuration; and responsive to a problem with the integrity of the first electrode configuration, switch to a different electrode configuration sufficient for use in ascertaining the patient's minute ventilation.

8. The stimulation device of claim 7, wherein the first electrode configuration comprises a ventricular bipolar configuration.

9. The stimulation device of claim 7, wherein the different electrode configuration comprises one or more of an atrial bipolar configuration and a dual unipolar configuration.

10. The stimulation device of claim 7, wherein the first electrode configuration comprises a bipolar configuration and the different electrode configuration comprises a unipolar configuration.

11. The stimulation device of claim 7, wherein the instructions cause the one or more processors to monitor the integrity of the first electrode configuration by monitoring one or more electrode impedances associated with leads that carry electrodes defining the first electrode configuration.

12. One or more computer-readable media having computer-readable instructions thereon which, when executed by one or more processors of a stimulation device, cause the one or more processors to:

establish a first electrode configuration sufficient for use in ascertaining a patient's minute ventilation;

ascertain the patient's minute ventilation using the first electrode configuration;

monitor the integrity of the first electrode configuration; and responsive to a problem with the integrity of the first electrode configuration, switch to a different electrode configuration sufficient for use in ascertaining the patient's minute ventilation.

13. A method for ascertaining minute ventilation comprising:

establishing a first electrode configuration using a stimulation device, the first electrode configuration being sufficient for use in ascertaining a patient's minute ventilation;

ascertaining the patient's minute ventilation using the first electrode configuration;

monitoring the integrity of the first electrode configuration;

responsive to a problem with the integrity of the first electrode configuration, automatically switching to a different electrode configuration sufficient for use in ascertaining the patient's minute ventilation; and using the different electrode configuration to ascertain the patient's minute ventilation.

14. The method of claim 13, wherein said establishing a first electrode configuration comprises establishing a ventricular bipolar configuration.

15. The method of claim 13, wherein said automatically switching to a different electrode configuration comprises automatically switching to one or more of an atrial bipolar configuration and a dual unipolar configuration.

16. The method of claim 13, wherein:

said establishing a first electrode configuration comprises establishing a bipolar configuration; and said automatically switching to a different electrode configuration comprises automatically switching to a unipolar configuration.

17. A method of ascertaining minute ventilation comprising:

defining priorities between multiple different minute ventilation electrode configurations;

establishing a minute ventilation electrode configuration in accordance with defined priorities;

ascertaining minute ventilation using the established minute ventilation electrode configuration;

monitoring the integrity of the established minute ventilation electrode configuration;

responsive to a problem with the integrity of the established minute ventilation electrode configuration, switching to a lower priority minute ventilation electrode configuration; and determining minute ventilation using the lower priority minute ventilation electrode configuration.

18. The method of claim 17, wherein the first-established minute ventilation electrode configuration comprises a ventricular bipolar configuration.

19. The method of claim 17, wherein the first-established minute ventilation electrode configuration comprises a atrial bipolar configuration.

20. The method of claim 17, wherein the first-established minute ventilation electrode configuration comprises a dual unipolar configuration.

21. The method of claim 17, wherein the lower priority minute ventilation electrode configuration comprises a atrial bipolar configuration.

22. The method of claim 17, wherein the lower priority minute ventilation electrode configuration comprises a dual unipolar configuration.

23. The method of claim 17, wherein the lower priority minute ventilation electrode configuration comprises a ventricular bipolar configuration.

24. The method of claim 17, wherein said monitoring comprises monitoring impedances associated with leads that carry electrodes defining the established electrode configuration.

25. One or more computer-readable media having computer-readable instructions thereon which, when executed by one or more processors, cause the processors to implement the method of claim 17.

26. A stimulation device comprising:

one or more computer-readable media;

multiple electrodes for stimulating and for monitoring minute ventilation;

one or more processors; and instructions stored on the computer-readable media which, when executed by the one or more processors, cause the processors to:

define priorities between multiple different minute ventilation electrode configurations;

establish a minute ventilation electrode configuration in accordance with defined priorities;

ascertain minute ventilation using the established minute ventilation electrode configuration;

monitor the integrity of the established minute ventilation electrode configuration;

responsive to a problem with the integrity of the established minute ventilation electrode configuration, switch to a lower priority minute ventilation electrode configuration; and determine minute ventilation using the lower priority minute ventilation electrode configuration.

27. A method of ascertaining minute ventilation comprising:

detecting a problem associated with an electrode configuration that is being utilized to ascertain minute ventilation for a rate-responsively paced heart patient, the electrode configuration having a first baseline impedance measure that is utilized to rate-responsively pace the patient;

stopping rate-responsive pacing that is based on minute ventilation;

automatically switching to a different electrode configuration;

re-establishing a baseline impedance measure that is associated with the different electrode configuration; and re-starting rate responsive pacing using the different electrode configuration to ascertain minute ventilation.

28. The method of claim 27, wherein said re-establishing the baseline impedance measure comprises doing so after the patient has been at rest for a pre-determined period of time.

29. The method of claim 27, wherein said re-establishing the baseline impedance measure comprises doing so using one or more activity sensors that monitor for a time period during which the patient's activity level is appropriate for re-establishing the baseline impedance.

30. The method of claim 27, wherein said re-establishing the baseline impedance measure comprises doing so by adapting a baseline impedance measure over a pre-determined period of time.

31. The method of claim 27, wherein said automatically switching comprises switching to an atrial bipolar configuration.

32. The method of claim 27, wherein said automatically switching comprises switching to a dual unipolar configuration.

33. The method of claim 27, wherein said automatically switching comprises switching to a bipolar configuration.

34. The method of claim 27, wherein said automatically switching comprises switching to a unipolar configuration.

35. The method of claim 27 further comprising storing, in device memory, information that indicates that an electrode configuration switch has taken place.

36. One or more computer-readable media having computer-readable instructions thereon which, when executed by one or more processors of a stimulation device, cause the one or more processors to:

detect a problem associated with an electrode configuration that is being utilized to ascertain minute ventilation for a rate-responsively paced heart patient, the electrode configuration having a first baseline impedance measure that is utilized to rate-responsively pace the patient;

stop rate-responsive pacing that is based on minute ventilation;

automatically switch to a different electrode configuration;

re-establish a baseline impedance measure that is associated with the different electrode configuration; and re-start rate responsive pacing using the different electrode configuration to ascertain minute ventilation.

37. A stimulation device comprising:

one or more computer-readable media;

multiple electrodes for stimulating and for monitoring minute ventilation;

one or more processors;

instructions stored on the computer-readable media which, when executed by the one or more processors, cause the processors to:

detect a problem associated with an electrode configuration that is being utilized to ascertain minute ventilation for a rate-responsively paced heart patient, the electrode configuration having a first baseline impedance measure that is utilized to rate-responsively pace the patient;

stop rate-responsive pacing that is based on minute ventilation;

automatically switch to a different electrode configuration;

re-establish a baseline impedance measure that is associated with the different electrode configuration; and re-start rate responsive pacing using the different electrode configuration to ascertain minute ventilation.

* * * * *